(12) United States Patent
Nakatsuji et al.

(10) Patent No.: US 8,981,163 B2
(45) Date of Patent: Mar. 17, 2015

(54) FLUORINE-CONTAINING AROMATIC COMPOUND AND METHOD FOR PRODUCING SAME

(75) Inventors: Junya Nakatsuji, Fujimino (JP); Makoto Matsuura, Ibaraki (JP); Kazuhiro Yamanaka, Tachikawa (JP)

(73) Assignee: Centrall Glass Company, Limited, Ube-shi (JP)

( * ) Notice: Subject to any disclaimer, the term of this patent is extended or adjusted under 35 U.S.C. 154(b) by 0 days.

(21) Appl. No.: 14/237,651

(22) PCT Filed: Aug. 8, 2012

(86) PCT No.: PCT/JP2012/070153
§ 371 (c)(1),
(2), (4) Date: Feb. 7, 2014

(87) PCT Pub. No.: WO2013/022015
PCT Pub. Date: Feb. 14, 2013

(65) Prior Publication Data
US 2014/0194655 A1    Jul. 10, 2014

(30) Foreign Application Priority Data

Aug. 9, 2011  (JP) ................................ 2011-173654
Aug. 2, 2012  (JP) ................................ 2012-171883

(51) Int. Cl.
| | | |
|---|---|---|
| C07C 39/367 | (2006.01) | |
| C07C 37/20 | (2006.01) | |
| C07C 39/19 | (2006.01) | |
| C07C 39/24 | (2006.01) | |

(52) U.S. Cl.
CPC .............. *C07C 39/19* (2013.01); *C07C 37/20* (2013.01); *C07C 39/24* (2013.01); *C07C 39/367* (2013.01)
USPC ............................ 568/763; 568/766; 568/769

(58) Field of Classification Search
None
See application file for complete search history.

(56) References Cited

U.S. PATENT DOCUMENTS

| | | | |
|---|---|---|---|
| 3,396,227 A * | 8/1968 | Gilbert .......................... 514/733 |
| 3,490,894 A | 1/1970 | Gilbert | |
| 6,459,004 B1 | 10/2002 | Ono et al. | |
| 7,001,707 B2 | 2/2006 | Hatakeyama et al. | |
| 7,125,943 B2 | 10/2006 | Sumida et al. | |
| 2002/0081499 A1 | 6/2002 | Zampini et al. | |
| 2011/0244188 A1 | 10/2011 | Komoriya et al. | |

FOREIGN PATENT DOCUMENTS

| | | |
|---|---|---|
| CN | 1302285 A | 7/2000 |
| JP | 2000-191576 A | 7/2000 |
| JP | 2004-83900 A | 3/2004 |
| JP | 2005-70531 A | 3/2005 |
| JP | 2009-108084 A | 5/2009 |
| JP | 2010-163604 A | 7/2010 |
| JP | 2010-235502 A | 10/2010 |
| WO | WO 01/02331 A1 | 1/2001 |

OTHER PUBLICATIONS

Wei-Fu Chen et al., "Generation and Synthetic Uses of Stable 4[2-lsopropylidene]-phenol Carbocation from Bisphenol A", 2004 American Chemical Society, Organic Letters 2004 vol. 6, No. 14, pp. 2341-2343.
International Search Report dated Sep. 4, 2012 with English translation (five (5) pages).
Kobayashi et al., "Studies on Organic Fluorine Compounds. XLIII. The Ene Reaction of Hexafluoroacetone," Chemical & Pharmaceutical Bulletin, 1984, pp. 5031-5035, vol. 32, No. 12.
Urry et al., "Multiple Multicenter Reactions of Perfluoro Ketones with Olefins," The Journal of Organic Chemistry, Jun. 1968, pp. 2302-2310, vol. 33, No. 6.
Japanese-language Written Opinion (PCT/ISA/237) dated Sep. 4, 2012 (four (4) pages).
Chinese Office Action dated Sep. 28, 2014 (7 pages).

* cited by examiner

*Primary Examiner* — Brian J Davis
(74) *Attorney, Agent, or Firm* — Crowell & Moring LLP

(57) ABSTRACT

Disclosed is a fluorine-containing aromatic compound represented by the following general formula (1) and its production method. In the formula (1), $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, n is an integer of 0 to 2, and each of m and l is independently 0 or 1. A polymer derived from this fluorine-containing aromatic compound contains —$C(CF_3)_2OH$ group at a position away from the polymer main chain. Therefore, it is useful for resist use.

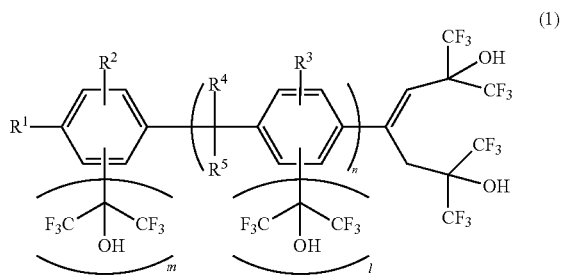

(1)

15 Claims, No Drawings

FLUORINE-CONTAINING AROMATIC COMPOUND AND METHOD FOR PRODUCING SAME

TECHNICAL FIELD

The present invention relates to a novel fluorine-containing aromatic compound and a method for producing the same. It relates to a novel fluorine-containing aromatic compound, and a method for producing the same, which is superior in adhesion to the substrate, when making a resist material prepared by its use with a photoacid generator, etc. after turning it into a polymerizable compound and then its polymerization, and which is for providing a precision resist pattern in lithography.

BACKGROUND OF THE INVENTION

Fluorine-containing compounds are used as functional materials by using characteristics such as having water repellency, low water absorption, high heat resistance, corrosion resistance, transparency, low dielectric constant, or low refractive index.

Hexafluoroisopropanol group is known as a functional group that provides particularly polyolefins, condensation-series polymers, etc. with an appropriate hydrophilicity in addition to low water absorption or transparency.

For example, polymer compounds having a hexafluoroisopropanol group(s), that is, a 2-hydroxy-1,1,1,3,3,3-hexafluoroisopropyl group(s), —C(CF$_3$)$_2$OH (in the following, may be referred to as HFIP group) are superior in adhesion to the substrate, when making a coating film by dissolving the polymer compounds in an organic solvent and then applying onto a glass substrate or the like. If the polymer compounds are used with a photoacid generator as resist compositions in photolithography, the difference of solubility in alkali developing solutions between exposed sections and unexposed sections after exposure becomes clear, thereby providing precision resist patterns. In recent years, the polymer compounds have been used as resist compositions to be exposed by an argon fluoride laser (wavelength: 193 nm). Photolithography refers to exposure of a substrate surface, on which a photoresist as a photosensitive material has been applied, to make desired patterns. Photolithography technique is a technique for forming a pattern made of a resist by the difference of solubility in the developing solution between exposed sections and unexposed sections of the resist.

Of the polymer compounds. HFIP group-containing phenols are subjected to selective nucleophilic substitution reactions in phenol moieties, thereby making polymerizable olefin monomers, such as acrylates, methacrylates, or vinyl ethers, by induced synthesis. The polymerizable olefin monomers are useful as resist compositions. Furthermore, it is possible to convert HFIP group-containing anilines into acrylic amides, methacrylic amides, vinyl amines, etc. by induced synthesis.

For example, Patent Publication 1 discloses the following fluorine-containing polymerizable monomer containing a HFIP group.

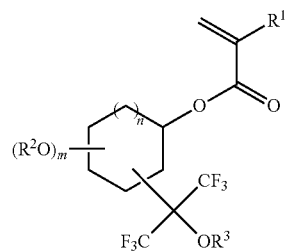

(1)

(In the formula, R$^1$ represents a hydrogen atom, a methyl group, a fluorine atom, or a trifluoromethyl group, n is 0 or 1, and m is an integer of 1 to (3+n). Each of R$^2$ and R$^3$ independently represents a hydrogen atom or a protecting group.)

Specifically, the following fluorine-containing polymerizable monomers, etc. are described.

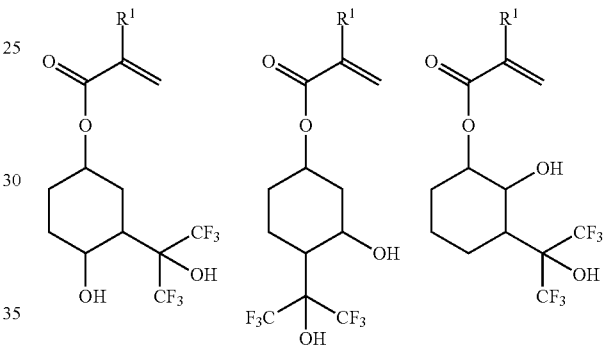

Polymer compounds containing units made up of at least these fluorine-containing polymerizable monomers, which have been prepared by polymerizing the fluorine-containing polymerizable monomers, are useful as resist compositions.

Furthermore. Patent Publication 2 discloses a method in which Compound B is nitrated to obtain Compound C, then Compound C is aminated to obtain Compound D, and then Compound D is converted to a phenol by adding a hydroxy group to obtain Compound E.

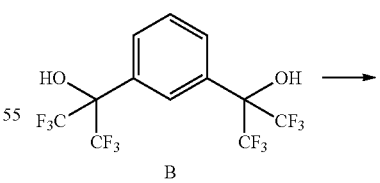

B

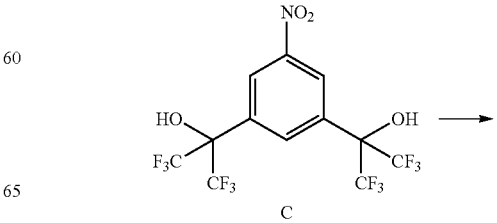

C

-continued

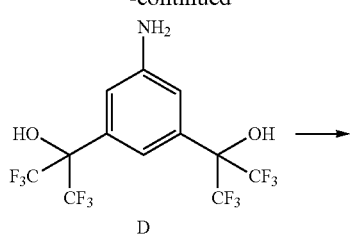
D

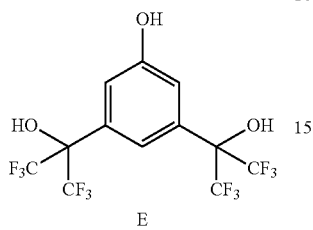
E

For example, Compound E is reacted and bonded with an acrylic acid, methacrylic acid or vinyl ether to produce fluorine-containing polymerizable monomers. Polymer compounds containing moieties made up of at least these fluorine-containing polymerizable monomers, which have been prepared by polymerizing the fluorine-containing polymerizable monomers, are useful as resist compositions.

The fluorine-containing polymerizable monomer described in Patent Publication 1, in which an HFIP group is away from a main chain of the polymer with an interposal of a cyclohexane ring, is easily produced. However, the compound described in Patent Publication 2 is synthesized by a multi-step reaction, having steps in the production.

In Examples 3-6 of Patent Publication 2, synthesis examples of the following compounds (F) to (I) prepared by introducing a double bond into the above compound (E) are specifically described. Since the compounds (F) to (I) have polymerizability, it is possible to make a resist by conducting a homopolymerization or a copolymerization with other polymerizable compounds, followed by adding a photoacid generator, etc.

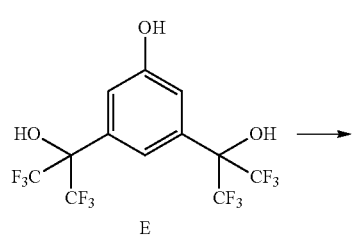
E

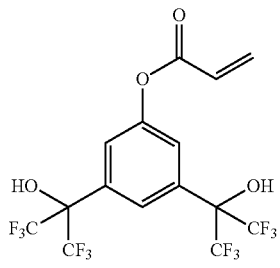
F

-continued

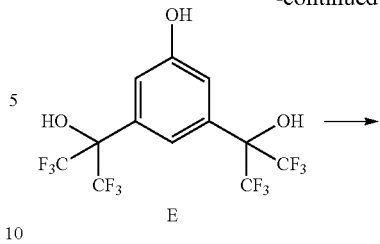
E

G

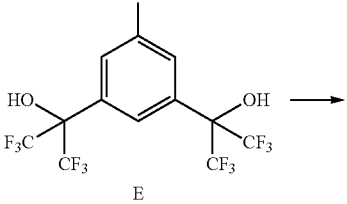
E

H

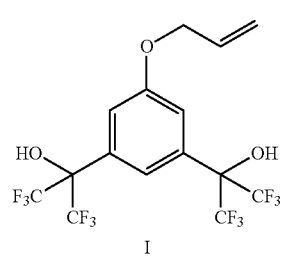
I

Furthermore, the following synthesis examples are described in Reference Examples 3-6 in Patent Publication 3.

Furthermore, in Non-patent Publication 1, there is described a reaction in which an isopropylidene bond (—C(CH$_3$)$_2$— moiety) of bisphenol A in the presence of sulfuric acid is cleaved by using the sulfuric acid as an acid catalyst.

PRIOR ART PUBLICATIONS

Patent Publications

Patent Publication 1: Japanese Patent Application Publication 2010-163604

Patent Publication 2: Japanese Patent Application Publication 2004-83900

Patent Publication 3: Japanese Patent Application Publication 2009-108084

Non-Patent Publications

Non-patent Publication 1: Organic Letters (2004), 6(14), 2341-2343

SUMMARY OF THE INVENTION

When a polymer resist, in which an HFIP group is away from a main chain of the polymer, is used with a photoacid generator as a resist composition, it is superior in adhesion to the substrate and the difference of solubility in alkali developing solutions between exposed sections and unexposed sections after exposure becomes clear, thereby providing precision resist patterns. In contrast with this, in a polymer resist having a structure in which an HFIP group is at a position in the vicinity of a main chain of the polymer, and in which there is a steric hindrance in the vicinity of the main chain, there has been a problem that it is not possible to sufficiently achieve the above-mentioned resist performance by containing the HFIP group.

It is an object of the present invention to provide a fluorine-containing aromatic compound, and its production method, as a raw material of an HFIP group-containing polymer, in which the HFIP group is at a position away from the polymer main chain, and which solves the above-mentioned problem and is produced by a simple method.

The present inventors have found that novel fluorine-containing aromatic compounds can be produced by a simple method from bisphenol A and other aromatic compounds, which have an isopropylidene bond, thereby reaching accomplishment of the present invention.

A cleavage reaction of an isopropylidene bond in aromatic compounds having an isopropylidene bond is known to occur by an inorganic acid such as sulfuric acid. By an eager study of the present inventors, we have found that there occurs a cleavage reaction of an isopropylidene bond that bonds an aromatic ring, in the presence of methanesulfonic acid or the like as an organic acid, and then, when hexafluoroacetone $((CF_3)_2C=O$, in the following it may be called HFA) is reacted. HFA is added, thereby obtaining a novel fluorine-containing aromatic compound having an HFIP group. With this, we have reached accomplishment of the invention.

The present invention includes fluorine-containing aromatic compounds of Inventions 1-7 and fluorine-containing aromatic compound production methods of Inventions 8-14 for obtaining the fluorine-containing aromatic compounds of Inventions 1-7.

[Invention 1]

A fluorine-containing aromatic compound represented by the general formula (1):

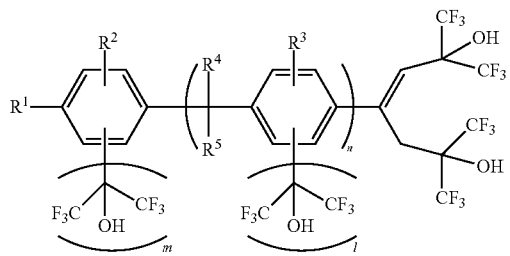

(In the formula (1), $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, n is an integer of 0 to 2, and each of m and l is independently 0 or 1).

[Invention 2]

The fluorine-containing aromatic compound of Invention 1, which is represented by the general formula (2):

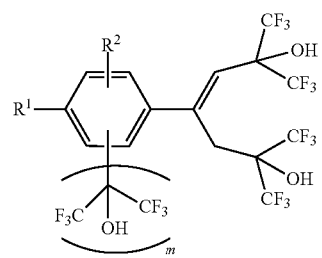

(In the formula (2). $R^1$ is a hydroxyl group or amino group, $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1).

[Invention 3]

The fluorine-containing aromatic compound of Invention 1 or Invention 2, which is represented by the general formula (3):

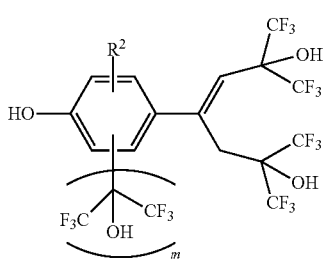

(In the formula (3), $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1).

[Invention 4]

The fluorine-containing aromatic compound of Inventions 1 to 3, which is represented by the formula (4):

(4)

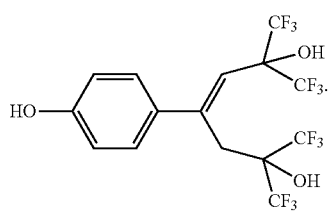

[Invention 5]
The fluorine-containing aromatic compound of Invention 1, which is represented by the general formula (5):

(5)

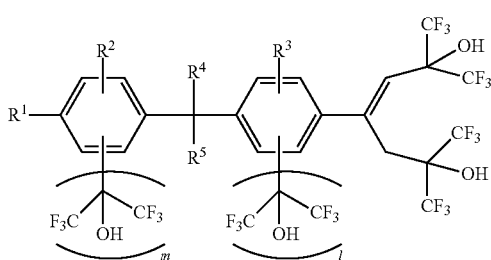

(In the formula (5), $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and 1 is independently 0 or 1).

[Invention 6]
The fluorine-containing aromatic compound of Invention 1 or Invention 5, which is represented by the general formula (6):

(6)

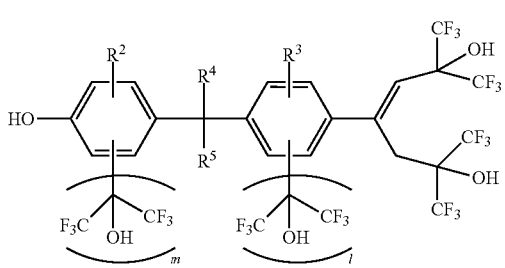

(In the formula (6), each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and 1 is independently 0 or 1).

[Invention 7]
The fluorine-containing aromatic compound of Invention 6, which is represented by the formula (7):

(7)

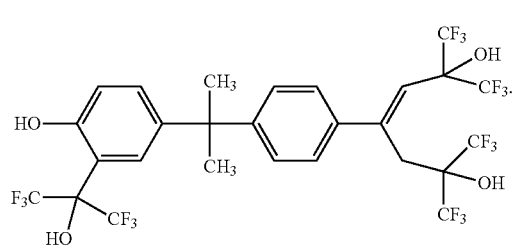

[Invention 8]
A method for producing a fluorine-containing aromatic compound represented by the general formula (1):

(1)

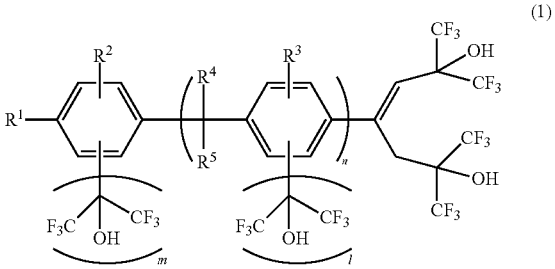

(In the formula (1), $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, n is an integer of 0 to 2, and each of m and 1 is independently 0 or 1.)

the method being characterized by that an aromatic compound represented by the general formula (8):

(8)

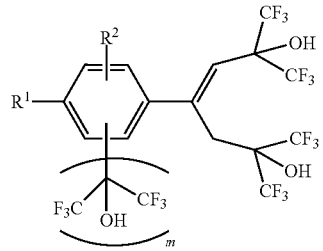

(In the formula (8). $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, $R^6$ is a hydroxyl group or amino group, and n is an integer of 0 to 2.)

is reacted with hexafluoroacetone in the presence of an acid catalyst.

The fluorine-containing aromatic compound of Invention 1, which is represented by the general formula (1), is synthesized by the production method of Invention 8.

[Invention 9]
The method for producing a fluorine-containing aromatic compound of Invention 8, which is represented by the general formula (2):

(2)

(In the formula (2), $R^1$ is a hydroxyl group or amino group, $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1.)

by reacting an aromatic compound represented by the general formula (9):

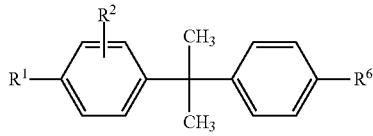
(9)

(In the formula (9). $R^1$ is a hydroxyl group or amino group, $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and $R^6$ is a hydroxyl group or amino group.) with hexafluoroacetone in the presence of an acid catalyst.

Thus, the fluorine-containing aromatic compound of Invention 2, which is represented by the general formula (2), is synthesized by the production method of Invention 9.

[Invention 10]

The method for producing a fluorine-containing aromatic compound of Invention 8 or Invention 9, which is represented by the general formula (3):

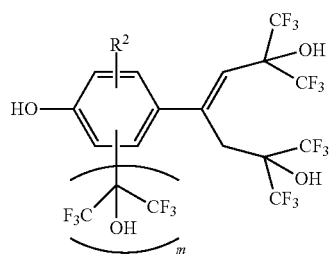
(3)

(In the formula (3). $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1.) by reacting an aromatic compound represented by the general formula (10):

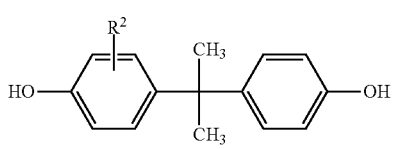
(10)

(In the formula (10). $R^2$ is a hydrogen atom, or a $C_{1-4}$ straight chain or a $C_3$ or $C_4$ branched chain alkyl group, and hydrogen atoms of the alkyl group may partially or totally be replaced with fluorine atoms.) with hexafluoroacetone in the presence of an acid catalyst.

It is possible to produce the fluorine-containing aromatic compound of Invention 3, which is represented by the general formula (3), by the production method of Invention 10.

[Invention 11]

The method for producing a fluorine-containing aromatic compound of Inventions 8-10, which is represented by the formula (4):

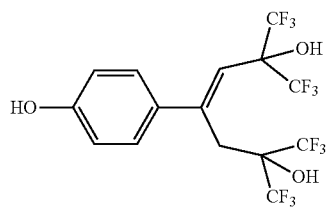
(4)

the method being characterized by reacting bisphenol A:

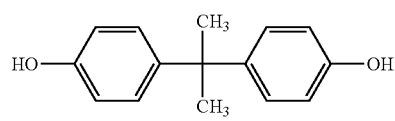 [SMILES: CC(C)(c1ccc(O)cc1)c1ccc(O)cc1]

with hexafluoroacetone in the presence of an acid catalyst.

Thus, it is possible to produce the fluorine-containing aromatic compound of Invention 4, which is represented by the formula (4), by the production method of Invention 11.

[Invention 12]

The method for producing a fluorine-containing aromatic compound of Invention 8, which is represented by the general formula (5):

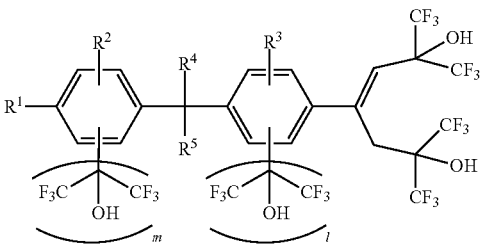
(5)

(In the formula (5), $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and 1 is independently 0 or 1.) by reacting an aromatic compound represented by the general formula (11):

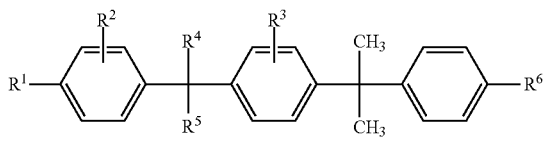
(11)

(In the formula (11). $R^1$ is a hydroxyl group or amino group, each of $R^2$ to $R^5$ is a hydrogen atom, or a $C_{1-4}$ straight chain or a $C_3$ or $C_4$ branched chain alkyl group, hydrogen atoms of the alkyl group may partially or totally be replaced with fluorine atoms, and $R^6$ is a hydroxyl group or amino group.) with hexafluoroacetone in the presence of an acid catalyst.

Thus, the fluorine-containing aromatic compound of Invention 5, which is represented by the general formula (5), is synthesized by the production method of Invention 12.

[Invention 13]

The method for producing a fluorine-containing aromatic compound of Invention 8 or Invention 12, which is represented by the general formula (6):

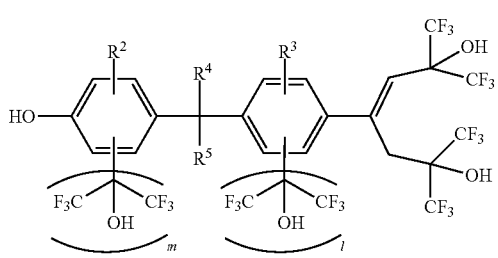
(6)

(In the formula (6), each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and l is independently 0 or 1.)

by reacting an aromatic compound represented by the general formula (12):

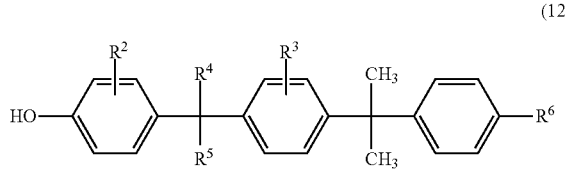
(12)

(In the formula (12), each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and $R^6$ is a hydroxyl group or amino group.)

with hexafluoroacetone in the presence of an acid catalyst.

Thus, it is possible to produce the fluorine-containing aromatic compound of Invention 6, which is represented by the general formula (6), by the method of Invention 13.

[Invention 14]

The method for producing a fluorine-containing aromatic compound of Invention 13, which is represented by the formula (7):

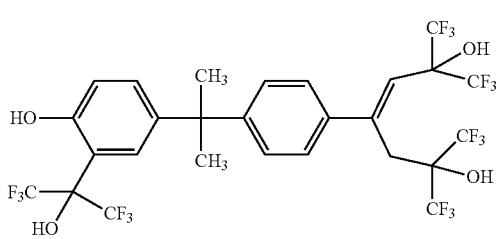
(7)

the method being characterized by reacting an aromatic compound represented by the formula (13):

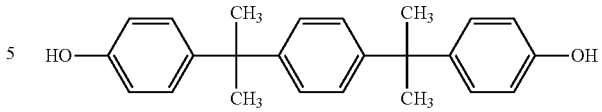
(13)

with hexafluoroacetone in the presence of an acid catalyst.

It is possible to produce the fluorine-containing aromatic compound of Invention 7, which is represented by the formula (7), by the production method of Invention 14.

[Invention 15]

The production method of Inventions 8-14, which is characterized by that the acid catalyst is methanesulfonic acid.

Advantageous Effect of the Invention

A novel fluorine-containing aromatic compound having an HFIP group(s) has been obtained by the fluorine-containing aromatic production method of the present invention, in which an isopropylidene bond of bisphenol A and aromatic compounds containing its derivatives is cleaved, and hexafluoroacetone is added. The fluorine-containing aromatic compound is useful for the resist use.

DETAILED DESCRIPTION

Fluorine-Containing Aromatic Compound

The fluorine-containing aromatic compound of the present invention contains an HFIP group(s) in the structure.

The present invention is a fluorine-containing aromatic compound represented by the general formula (1):

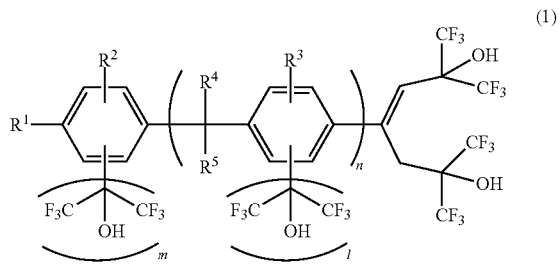
(1)

(In the formula (1), $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, n is an integer of 0 to 2, and each of m and l is independently 0 or 1.).

For the use as a resist material, it is preferable that $R^1$ is a hydroxy group or amino group. In the fluorine-containing aromatic compound represented by the general formula (1), if $R^1$ is a hydroxyl group, it is possible to introduce a functional group having a double bond into the moiety of the hydroxyl group by the method mentioned in Patent Publication 2 and Patent Publication 3. With this, it can be converted to a polymerizable compound. The polymerizable compound is reacted with acrylic acid, methacrylic acid or vinyl ether to make a fluorine-containing polymerizable monomer, followed by polymerization with another functional monomer, etc. to make a polymer and then adding a photoacid generator. With this, it is possible to make a photoresist. The double bond on the side of the HFIP group has a low reactivity, but the double bond of a functional group formed by replacing the hydrogen atom of the hydroxy group tends to undergo the polymerization reaction.

As the fluorine-containing aromatic compound represented by the general formula (1) is specifically exemplified, it is possible to mention the following compounds. The present invention is, however, not limited to these.

[Phenols]

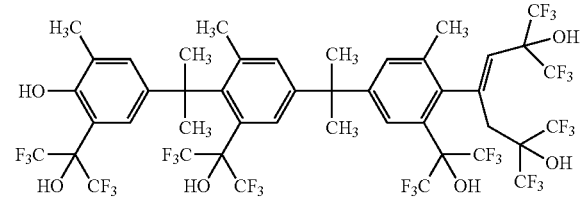

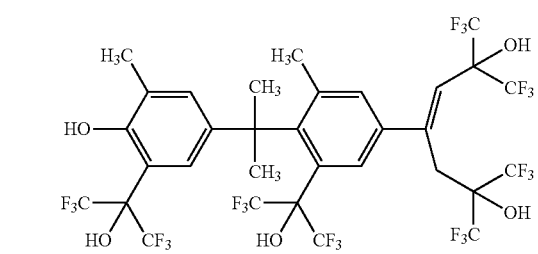

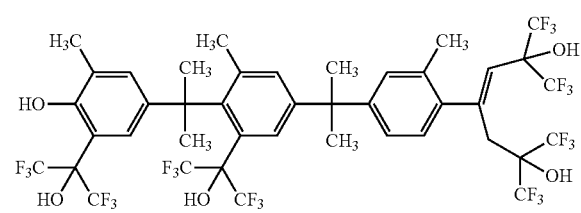

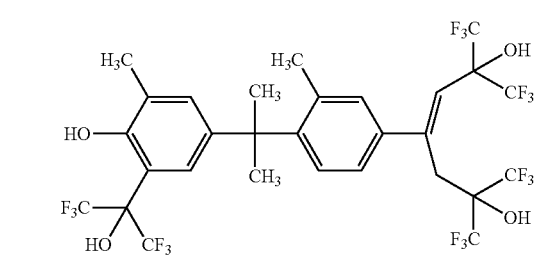

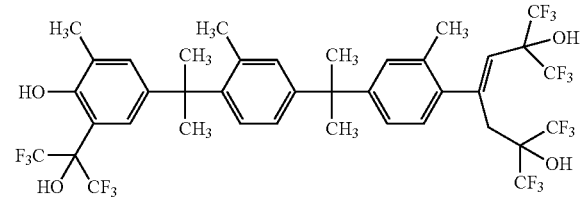

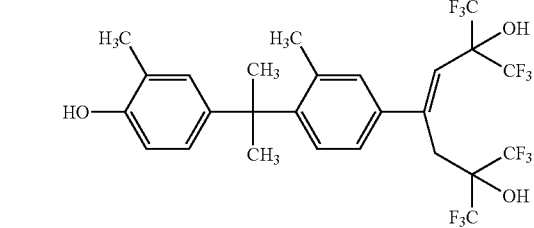

-continued

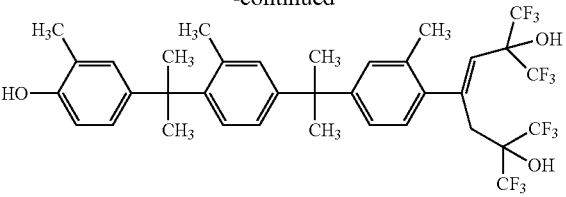

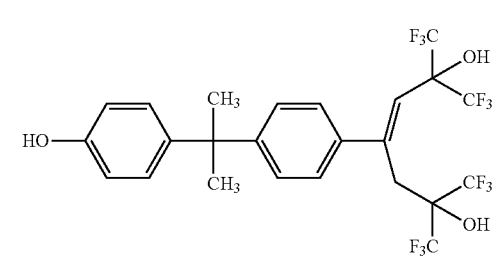

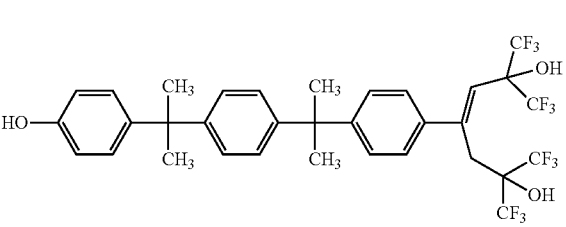

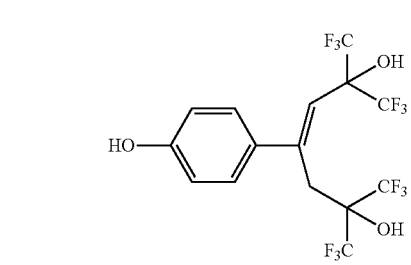

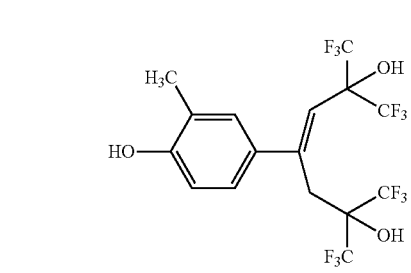

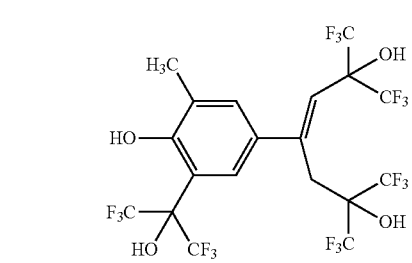

[Amines]

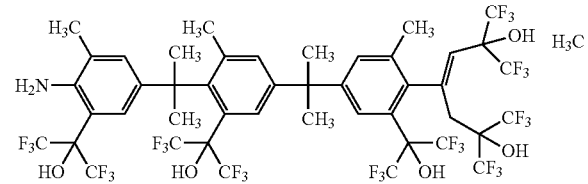

-continued

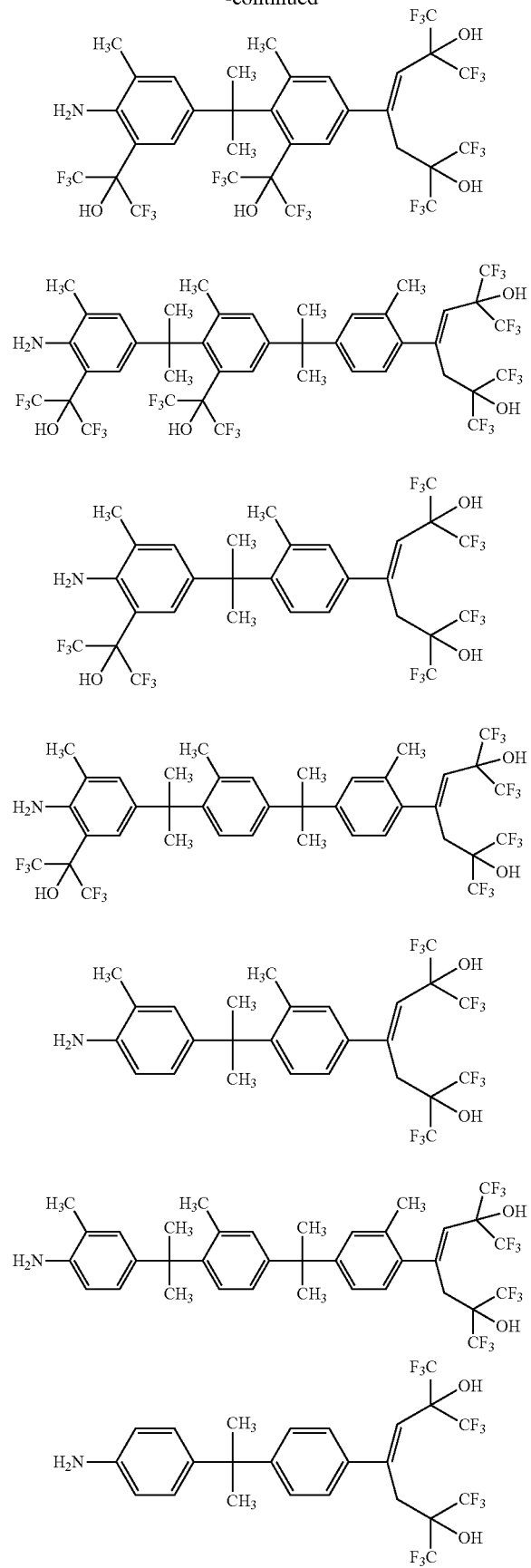

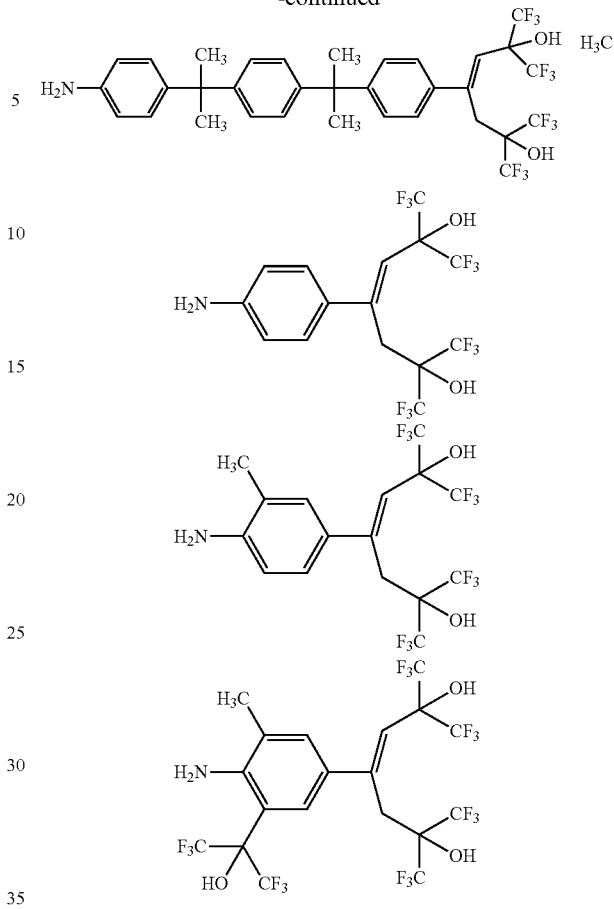

Of the fluorine-containing aromatic compounds represented by the general formula (1), a fluorine-containing aromatic compound represented by the general formula (2):

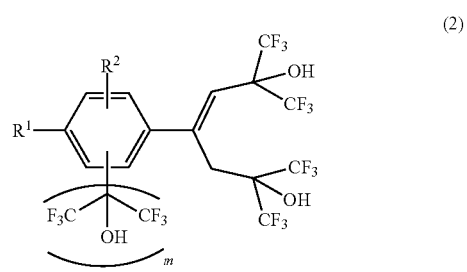

(2)

(In the formula (2), $R^1$ is a hydroxyl group or amino group, $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1.) is easily synthesized. Since it has one aromatic ring, when using it as a raw material of a resist composition, the resist to be obtained is easily soluble in organic solvents. Therefore, its handling is good in photolithography.

Furthermore, when making a fluorine-containing polymerizable monomer, it is preferable that $R^1$ is OH group. By the method mentioned in Patent Publication 2 and Patent Publication 3, a functional group having a double bond can be introduced into the moiety of the hydroxy group to make a polymerizable compound, and then it can be reacted with acrylic acid or methacrylic acid, etc.

By the above-mentioned reason, a fluorine-containing aromatic compound represented by the general formula (3):

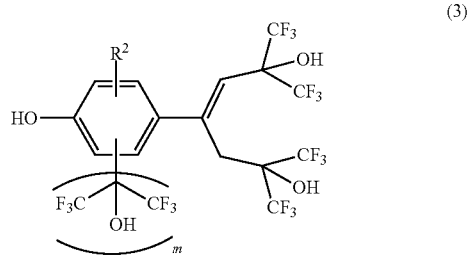

(3)

(In the formula (3), $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1.) is preferable.

Of the fluorine-containing aromatic compounds represented by the formula (3), it is possible to mention a fluorine-containing aromatic compound represented by the formula (4):

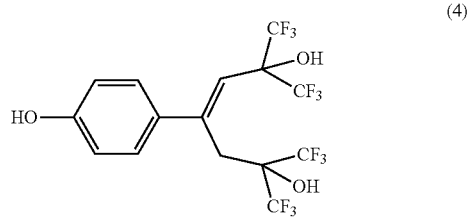 [SMILES: Oc1ccc(/C(=C/C(O)(C(F)(F)F)C(F)(F)F)CC(O)(C(F)(F)F)C(F)(F)F)cc1]

(4)

as a particularly preferable fluorine-containing aromatic compound.

Furthermore, of the fluorine-containing aromatic compounds represented by the general formula (1), a fluorine-containing aromatic compound represented by:

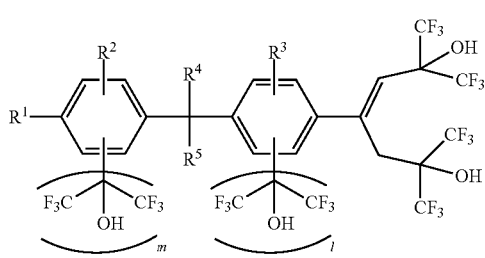

(5)

(In the formula (5), $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and l is independently 0 or 1.) is easily synthesized. Since it contains two aromatic rings, when using it as a raw material of a resist composition, the resist to be obtained is easily soluble in organic solvents. Therefore, its handling is good in photolithography.

Furthermore, when making a fluorine-containing polymerizable monomer, it is preferable that $R^1$ is OH group. By the method mentioned in Patent Publication 2 and Patent Publication 3, a functional group having a double bond can be introduced into the moiety of the hydroxy group to make a polymerizable compound, and then it can be reacted with acrylic acid or methacrylic acid, etc.

By the above-mentioned reason, a fluorine-containing aromatic compound represented by the general formula (6):

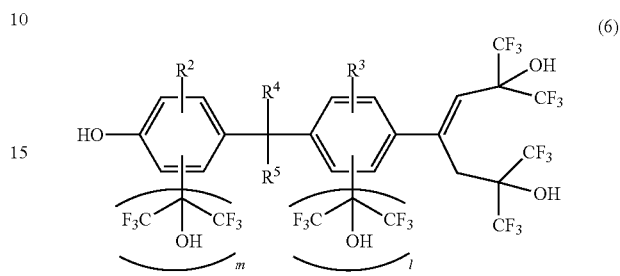

(6)

(In the formula (6), each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and l is independently 0 or 1.) is preferable.

Of the aromatic compounds represented by the formula (6), it is possible to mention a fluorine-containing aromatic compound represented by the formula (7):

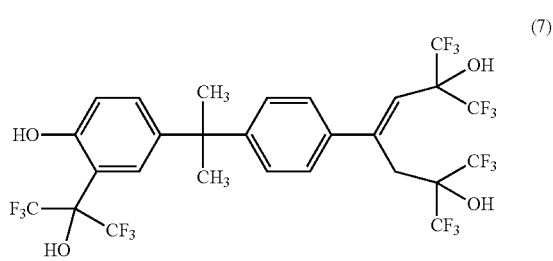 [SMILES: CC(C)(c1ccc(/C(=C/C(O)(C(F)(F)F)C(F)(F)F)CC(O)(C(F)(F)F)C(F)(F)F)cc1)c1ccc(O)c(C(O)(C(F)(F)F)C(F)(F)F)c1]

(7)

as a particularly preferable compound.

[Raw Material (Reactant) of the Fluorine-Containing Aromatic Compound]

The fluorine-containing aromatic compound represented by the general formulas (1) to (3), the formula (4), the general formula (5) or (6), or the formula (7) is respectively synthesized by reacting the compounds represented by the general formulas (8) to (10), bisphenol A, or the aromatic compounds represented by the general formula (11) or (12) or the formula (13) as the raw material (reactant) with hexafluoroacetone in the presence of an acid catalyst.

As the aromatic compound represented by the general formula (8):

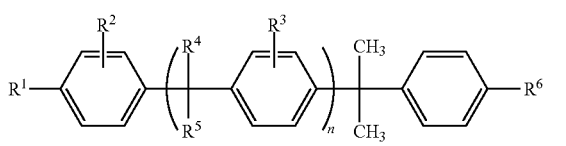

(8)

(In the formula (8). $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, $R^6$ is a hydroxyl group or amino group, and n is an integer of 0 to 2.) is specifically exemplified, it is possible to mention the following compounds. The present invention is, however, not limited to these.

[Phenols]

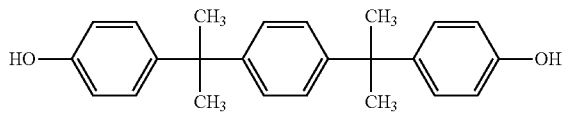

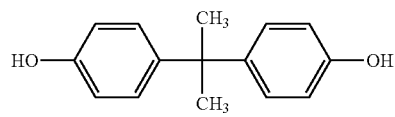

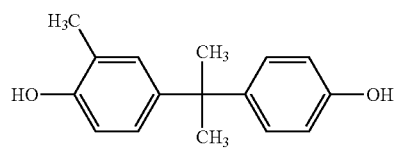

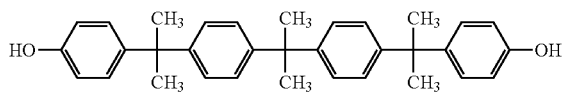

[Amines]

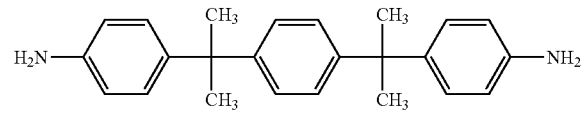

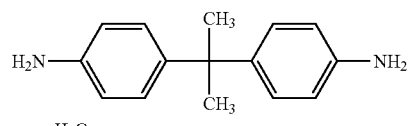

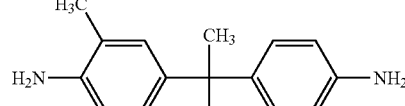

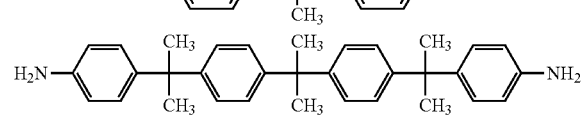

Of the aromatic compounds represented by the general formula (8), when using the compound represented by the general formula (9):

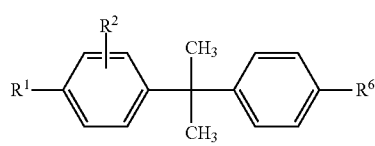

(9)

(In the formula (9). $R^1$ is a hydroxyl group or amino group, $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and $R^a$ is a hydroxyl group or amino group.)

the fluorine-containing aromatic compound represented by the general formula (2) is easily synthesized. Since the fluorine-containing aromatic compound represented by the general formula (2) has one aromatic ring, when using it as a raw material of a resist composition, the resist to be obtained is easily soluble in organic solvents. Therefore, its handling is good in photolithography.

Furthermore, when making a fluorine-containing polymerizable monomer by a reaction with acrylic acid or methacrylic acid, etc., it is preferable that $R^1$ and $R^6$ are OH groups. It is preferable to use an aromatic compound represented by the general formula (10):

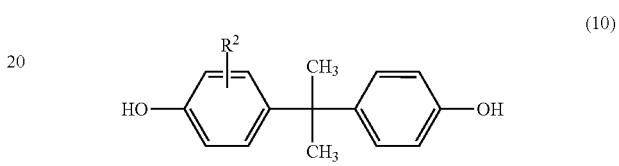

(10)

(In the formula (10), $R^2$ is a hydrogen atom, or a $C_{1-4}$ straight chain or a $C_3$ or $C_4$ branched chain alkyl group, and hydrogen atoms of the alkyl group may partially or totally be replaced with fluorine atoms.)

Of the aromatic compounds represented by the formula (10), it is possible to mention bisphenol A as a particularly preferable aromatic compound.

Of the aromatic compounds represented by the general formula (8), when using the compound represented by the general formula (11):

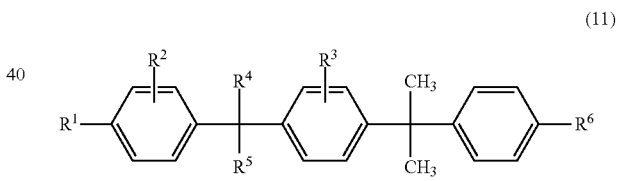

(11)

(In the formula (11), $R^1$ is a hydroxyl group or amino group, each of $R^2$ to $R^5$ is a hydrogen atom, or a $C_{1-4}$ straight chain or a $C_3$ or $C_4$ branched chain alkyl group, hydrogen atoms of the alkyl group may partially or totally be replaced with fluorine atoms, and $R^6$ is a hydroxyl group or amino group.) the fluorine-containing aromatic compound represented by the general formula (6) is easily synthesized. Since the fluorine-containing aromatic compound represented by the general formula (6) has two aromatic rings, when using it as a raw material of a resist composition, the resist to be obtained is easily soluble in organic solvents. Therefore, its handling is good in photolithography.

Furthermore, when making a fluorine-containing polymerizable monomer, it is preferable that $R^1$ is OH group. By the method mentioned in Patent Publication 2 and Patent Publication 3, a functional group having a double bond can be introduced into the moiety of the hydroxy group to make a polymerizable compound, and then it can be reacted with acrylic acid or methacrylic acid, etc.

By the above-mentioned reason, it is preferable that $R^1$ is OH group. Therefore, it is preferable to use a compound represented by the general formula (12):

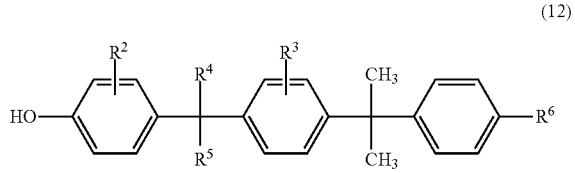

(12)

(In the formula (12), each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and $R^6$ is a hydroxyl group or amino group.)

Of the aromatic compounds represented by the formula (12), it is possible to mention an aromatic compound represented by the formula (13):

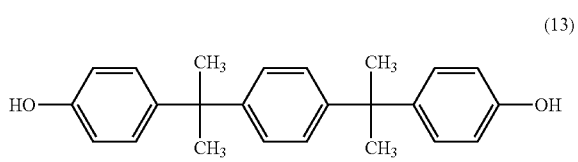 [SMILES: CC(C)(c1ccc(O)cc1)c1ccc(C(C)(C)c2ccc(O)cc2)cc1]

(13)

as a particularly preferable aromatic compound.

[Method for Producing the Fluorine-Containing Aromatic Compound]

The production method of the present invention for obtaining a novel fluorine-containing aromatic compound having an HFIP group(s) is one in which in the presence of an acid catalyst an isopropylidene bond in an aromatic compound is cleaved by the acid catalyst, and then HFA is added, thereby obtaining an HFIP group(s).

The method for producing the fluorine-containing aromatic compound of the present invention described in Inventions 8 to 14 is explained in detail in the following by using the method for producing 1,1,1,7,7,7-hexafluoro-4-(4-hydroxyphenyl)-2,6-bis(trifluoromethyl)hept-3-yne-2,6-diol as an example.

The method for producing the fluorine-containing aromatic compound of the present invention is not limited to the fluorine-containing aromatic compound production method of Invention 11 for synthesizing the fluorine-containing aromatic compound represented by the formula (4).

The fluorine-containing aromatic compound represented by the formula (4) is obtained by reacting bisphenol A with HFA or HFA trihydrate.

As it is specifically shown, when bisphenol A was reacted with HFA in the presence of methanesulfonic acid ($CH_3SO_3H$), as shown in the following, there was obtained a fluorine-containing aromatic compound containing HFIP groups and represented by the formula (4).

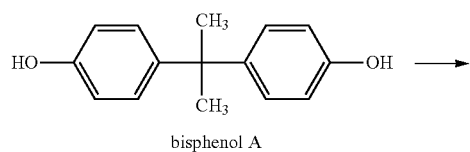

bisphenol A

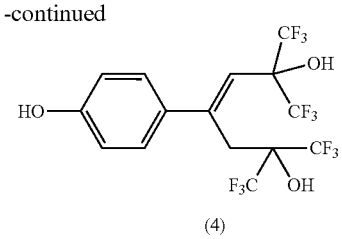

(4)

As the reaction mechanism of the present reaction is assumed, as shown by the following reaction scheme, an isopropylidene bond contained in bisphenol A is cleaved. Then, HFA is added to form HFIP groups. With this, it was assumed that the fluorine-containing aromatic compound containing HFIP groups represented by the formula (4) had been obtained.

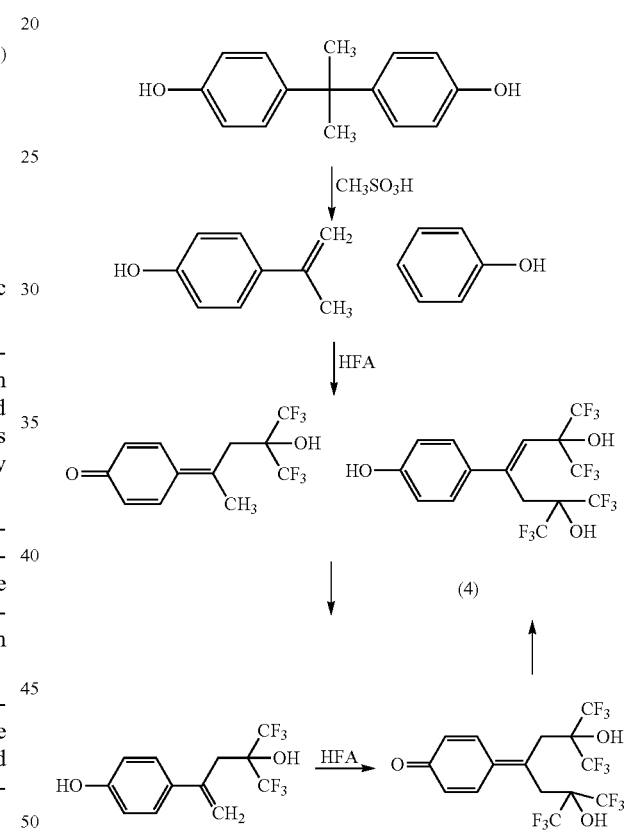

When synthesizing the fluorine-containing aromatic compound of the present invention, since boiling point of HFA is −28° C., in order to keep HFA in the reaction system, it is preferable to use a cooling apparatus or a sealed reactor. In particular, it is preferable to use a sealed reactor.

Furthermore, when using HFA trihydrate, the reaction is conducted by mixing bisphenol A with HFA trihydrate. Since boiling point of HFA trihydrate is 105° C., its handing is easier than that of HFA. Upon this, the reaction apparatus may be a sealed reactor. By conducting a water cooling using a reflux condensing tube, it is possible to keep the HFA trihydrate in the reaction system.

It is preferable that the amount of HFA or HFA trihydrate used when synthesizing the fluorine-containing aromatic compound of the present invention is from 2 mol equivalents to 5 mol equivalents, preferably from 2 mol equivalents to 3 mol equivalents, relative to bisphenol A. If it is less than 2 mol equivalents, yield of the fluorine-containing aromatic compound represented by the formula (4) is low. Even if it is used by exceeding 5 mol equivalents, the reaction progresses, and the fluorine-containing aromatic compound represented by the formula (4) is obtained. It is, however, not necessary to use that by exceeding 5 mol equivalents.

The reaction when synthesizing the fluorine-containing aromatic compound of the present invention can be conducted in a temperature range of from 50° C. to 200° C. From 60° C. to 130° C. is particularly preferable. At a temperature lower than 50° C., the progress of the reaction is difficult. At a temperature higher than 200° C., particularly at 250° C. or higher, yield of the fluorine-containing aromatic compound represented by the formula (4) lowers.

As the catalyst used. Lewis acid such as aluminum chloride, iron (III) chloride or boron fluoride, and organic sulfonic acid such as benzenesulfonic acid, camphorsulfonic acid (CSA), methanesulfonic acid, p-toluenesulfonic acid (pTsOH), p-toluenesulfonic acid (pTsOH) monohydrate or pyridinium p-toluene sulfonate (PPTS) are preferable. Of these, aluminum chloride, iron (III) chloride, methanesulfonic acid and p-toluenesulfonic acid (pTsOH) monohydrate are preferable. Particularly, methanesulfonic acid is preferable. The amount of the catalyst used is from 1 mol % to 50 mol %, preferably 3 mol % to 40 mol %, relative to 100 mol % of bisphenol A. If it is less than 1 mol %, yield of the fluorine-containing aromatic compound represented by formula (4) is low. Even if it is used by exceeding 50 mol %, the reaction progresses. It is, however, not necessary to add more than that.

Although the reaction can be conducted without using solvent, it is preferable to use solvent. With this, handling is good. The solvent to be used is not particularly limited as long as it is not involved in the reaction. An aromatic hydrocarbon, such as xylene, toluene, benzene, anisole, diphenyl ether, nitrobenzene or benzonitrile, a chlorine-series solvent, such as chloroform, methylene chloride, dichloroethane or dichlorobenzene, water, or hexafluoroisopropanol ((CF$_3$)$_2$HC—OH) is preferable. The amount of the solvent to be used is not particularly limited, but use in a large amount is not preferable since yield of the fluorine-containing aromatic compound represented by the general formula (4) per unit volume of the reactor decreases.

In the case of conducting the reaction in a sealed reactor (autoclave), the mode is different depending on the use of HFA or HFA trihydrate. In the case of using HFA, the reactor is charged firstly with bisphenol A and catalyst or solvent. Then, it is preferable to add HFA, while increasing the temperature in a manner that the reactor inside pressure does not exceed 0.5 MPa.

In the case of using HFA trihydrate, it is possible to conduct the reaction by firstly introducing bisphenol A and HFA trihydrate into the reactor and then adding catalyst or solvent.

Although the reaction time of the reaction is not particularly limited, it is suitably selected depending on the temperature or the amount of catalyst used, etc. Therefore, it is preferable to terminate the reaction, after confirming that the raw material has sufficiently been consumed by a general-purpose analysis means such as gas chromatography. After the termination of the reaction, it is possible to obtain the fluorine-containing aromatic compound represented by the formula (4) by means such as extraction, distillation and crystallization. Furthermore, according to need, it is possible to purify the fluorine-containing aromatic compound represented by the formula (4) by column chromatography or recrystallization, etc.

Furthermore, as the reaction mechanism of the present reaction in the case of amino group is assumed, as shown by the following reaction scheme, isopropylidene group in 2,2-bis(p-aminophenyl)propane is cleaved in the presence of methanesulfonic acid. Then, HFA is continuously subject to an addition reaction to generate HFIP groups. With this, it is assumed that the fluorine-containing aromatic compound represented by the formula (10) was obtained.

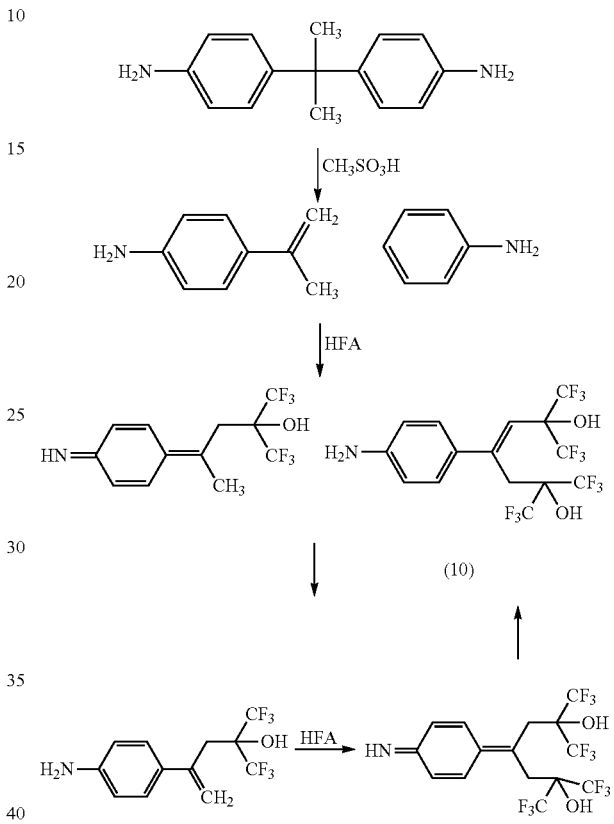

As mentioned above, the fluorine-containing aromatic compound having an HFIP group(s) of the present invention, which is obtained by the fluorine-containing aromatic compound production method of the present invention, can be produced by a simple method by using as the raw material an aromatic compound having an isopropylidene bond, which includes bisphenol A or its derivative. In particular, a fluorine-containing aromatic compound of the present invention, which is derived from bisphenol A with a low price, is more easily produced and more useful as compared with conventional fluorine-containing compounds used in photoresist.

Furthermore, it is possible to introduce a functional group having a double bond into the fluorine-containing aromatic compound having an HFIP group(s) of the present invention by the method mentioned in Patent Publication 2 and Patent Publication 3 to make a fluorine-containing polymerizable monomer, followed by polymerization to make a polymer compound. By using this as a resist composition, the HFIP group(s) is at a position away from the polymer main chain. Therefore, there is a possibility to obtain a superior resist.

EXAMPLES

Although examples of the present invention are specifically shown, the present invention is not limited to the following examples.

Identification methods of the synthesized fluorine-containing aromatic compounds are shown in the following (1) and (2).

(1) NMR (Nuclear Magnetic Resonance) Measurement

By using a nuclear magnetic resonance apparatus (made by JEOL, Ltd.) with a resonance frequency of 400 MHz, the measurements of $^1$H-NMR and $^{19}$F-NMR were conducted.

(2) DI-MS (Mass Spectrometry Spectrum) Measurement

By using a mass spectrometer (made by JEOL, Ltd.; product number: JMS-T100GC), the mass spectrometry spectrum was measured.

Example 1

Synthesis of a fluorine-containing aromatic compound represented by the structural formula (4) (1,1,1,7,7,7-hexafluoro-4-(4-hydroxyphenyl)-2,6-bis(trifluoromethyl)hept-3-yne-2,6-diol)

At room temperature (20° C.), a stainless steel autoclave was charged with 50 g (0.21 mol) of bisphenol A, 200 g of hexafluoroisopropanol, and 1 g (2 mass % relative to bisphenol A) of methanesulfonic acid as an acid catalyst. After adding 80 g (0.48 mol) of hexafluoroacetone (HFA), the temperature was gradually increased, and stirring was conducted at 55° C. for 8 hours to make the following reaction proceed. After termination of the reaction, hexafluoroisopropanol as the solvent was distilled out, thereby obtaining a solid. By conducting NMR and mass spectrometry, it was confirmed that a fluorine-containing aromatic compound represented by the formula (4) was obtained at a high yield of 98% relative to theoretical yield. That is, a fluorine-containing aromatic compound represented by the formula (4) was obtained at a high purity.

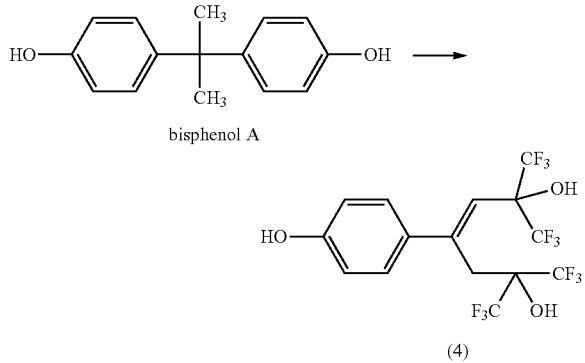

The results of mass spectrometry of $^1$H-NMR measurement and $^{19}$F-NMR measurement on the solid are shown in the following.

$^1$H-NMR (solvent: d-DMSO, TMS): δ3.63 (2H, s), 5.49 (1H, s), 6.71 (2H, d, J=85 Hz), 7.16 (2H, d, J=8.5 Hz), 9.58 (1H, s)

$^{19}$F-NMR (solvent, d-DMSO, CCl$_3$F): δ−74.8 (6F, s), −73.4 (6F, s)

Mass: (m/z) 466.04 (M$^+$)

Example 2

Synthesis of a Fluorine-Containing Aromatic Compound Represented by the Structural Formula (7)

At room temperature (20° C.), a stainless steel autoclave was charged with 15 g (0.04 mol) of the compound (13), 200 g of hexafluoroisopropanol, and 0.3 g (2 mass % relative to the compound (13)) of methanesulfonic acid as an acid catalyst. After adding 28.7 g (0.17 mol) of HFA, the temperature was gradually increased, and stirring was conducted at 55° C. for 8 hours to make the following reaction proceed. After termination of the reaction, hexafluoroisopropanol as the solvent was distilled out, thereby obtaining a solid. By conducting NMR and mass spectrometry, it was confirmed that a fluorine-containing aromatic compound represented by the formula (7) was obtained at a high yield of 80 mass % relative to theoretical yield. That is, a fluorine-containing aromatic compound represented by the formula (7) was obtained at a high purity.

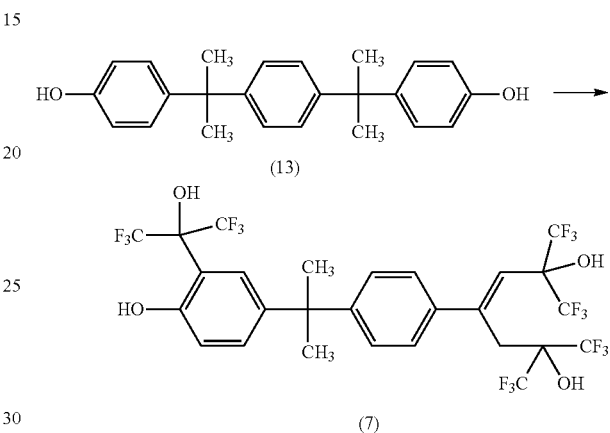

The results of mass spectrometry of $^1$H-NMR measurement and $^{19}$F-NMR measurement on the solid are shown in the following.

$^1$H-NMR (solvent, deuterated acetone. TMS): 2.03 (6H, s), 7.01 (4H, m), 7.40 (4H, m), 8.31 (1H, s), 10.36 (1H, s)

$^{19}$F-NMR (solvent, deuterated acetone, CCl$_3$F): −74.8 (6F, s), −74.9 (12F, s)

Mass: (m/z) 750.14 (M$^+$)

The invention claimed is:

1. A fluorine-containing aromatic compound represented by the general formula (1):

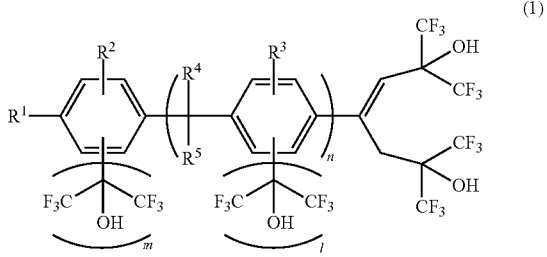

wherein R$^1$ is a hydroxyl group or amino group, each of R$^2$ to R$^5$ is independently a hydrogen atom, or a C$_{1-4}$ straight chain or a C$_3$ or C$_4$ branched chain alkyl group, hydrogen atoms of the alkyl group may partially or totally be replaced with fluorine atoms, n is an integer of 0 to 2, and each of m and 1 is independently 0 or 1.

2. The fluorine-containing aromatic compound as claimed in claim 1, which is represented by the general formula (2):

(2)

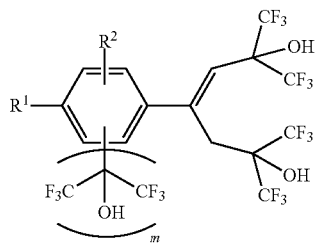

wherein $R^1$ is a hydroxyl group or amino group, $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1.

3. The fluorine-containing aromatic compound as claimed in claim 1, which is represented by the general formula (3):

(3)

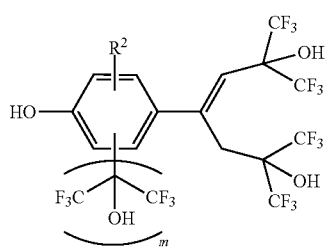

wherein $R^2$ is a hydrogen atom, or a $C_{1-4}$ straight chain or a $C_3$ or $C_4$ branched chain alkyl group, hydrogen atoms of the alkyl group may partially or totally be replaced with fluorine atoms, and m is 0 or 1.

4. The fluorine-containing aromatic compound as claimed in claim 1, which is represented by the formula (4):

(4)

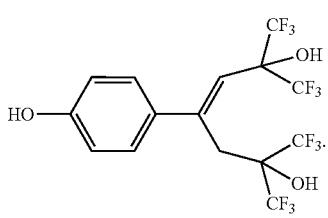

5. The fluorine-containing aromatic compound as claimed in claim 1, which is represented by the general formula (5):

(5)

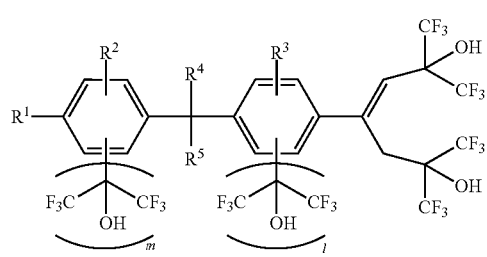

wherein $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and l is independently 0 or 1.

6. The fluorine-containing aromatic compound as claimed in claim 1, which is represented by the general formula (6):

(6)

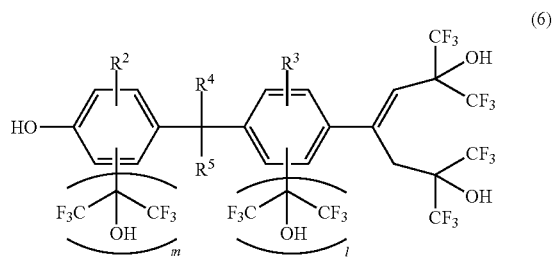

wherein each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, and each of m and l is independently 0 or 1.

7. The fluorine-containing aromatic compound as claimed in claim 6, which is represented by the formula (7):

(7)

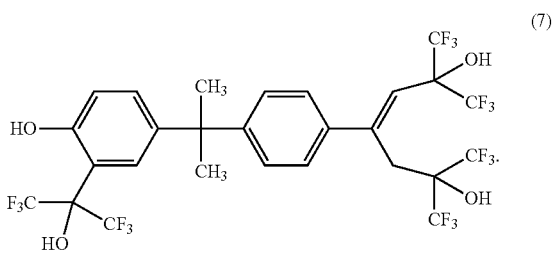 [SMILES: CC(C)(c1ccc(/C(=C/C(O)(C(F)(F)F)C(F)(F)F)CC(O)(C(F)(F)F)C(F)(F)F)cc1)c1ccc(O)c(C(O)(C(F)(F)F)C(F)(F)F)c1]

8. A method for producing a fluorine-containing aromatic compound represented by the general formula (1):

(1)

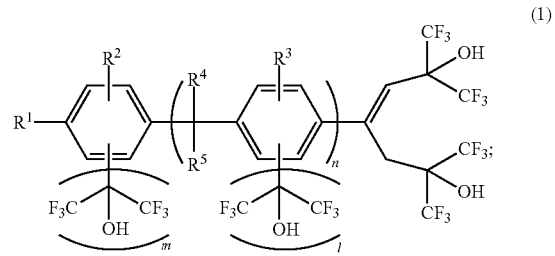

wherein an aromatic compound represented by the general formula (8):

(8)

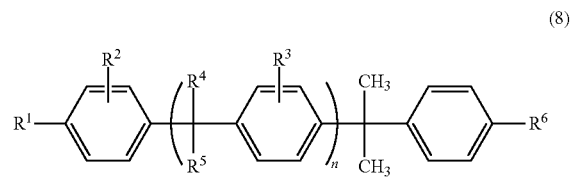

is reacted with hexafluoroacetone in the presence of an acid catalyst;

wherein $R^1$ is a hydroxyl group or amino group, each of $R^2$ to $R^5$ is independently a hydrogen atom, or a $C_{1-4}$ straight chain or a $C_3$ or $C_4$ branched chain alkyl group, hydrogen atoms of the alkyl group may partially or totally be replaced with fluorine atoms, $R^6$ is a hydroxyl group or amino group, n is an integer of 0 to 2, and each of m and 1 is independently 0 or 1.

9. The method for producing a fluorine-containing aromatic compound as claimed in claim 8, which is represented by the general formula (2):

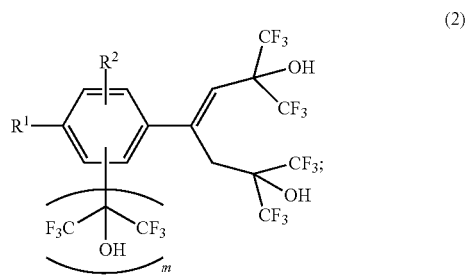

(2)

wherein an aromatic compound represented by the general formula (9):

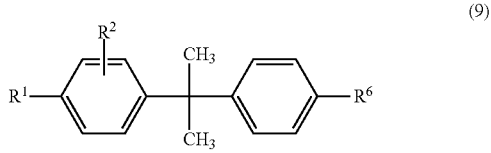

(9)

is reacted with hexafluoroacetone in the presence of an acid catalyst;
wherein $R^1$ is a hydroxyl group or an amino group; $R^2$ is a hydrogen atom, a $C_{1-4}$ straight chain, or a $C_3$ or $C_4$ branched chain alkyl group, wherein hydrogen atoms of the alkyl groups may partially or totally be replaced with fluorine atoms; $R^6$ is a hydroxyl group or an amino group; and m is 0 or 1.

10. The method for producing a fluorine-containing aromatic compound as claimed in claim 8, which is represented by the general formula (3):

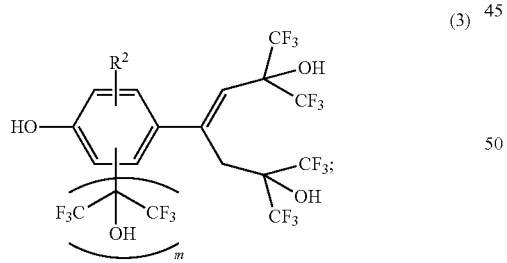

(3)

wherein an aromatic compound represented by the general formula (10):

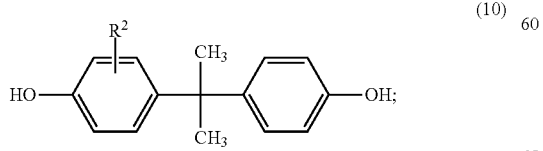

(10)

is reacted with hexafluoroacetone in the presence of an acid catalyst;

wherein $R^2$ is a hydrogen atom, a $C_{1-4}$ straight chain, or a $C_3$ or $C_4$ branched chain alkyl group, wherein hydrogen atoms of the alkyl groups may partially or totally be replaced with fluorine atoms; and m is 0 or 1.

11. The method for producing a fluorine-containing aromatic compound as claimed in claim 8, which is represented by the formula (4):

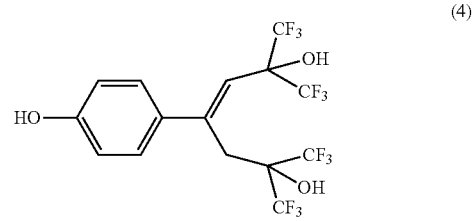 [SMILES: Oc1ccc(/C(=C/C(O)(C(F)(F)F)C(F)(F)F)CC(O)(C(F)(F)F)C(F)(F)F)cc1]

(4)

wherein bisphenol A:

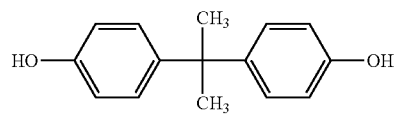

is reacted with hexafluoroacetone in the presence of an acid catalyst.

12. The method for producing a fluorine-containing aromatic compound as claimed in claim 8, which is represented by the general formula (5):

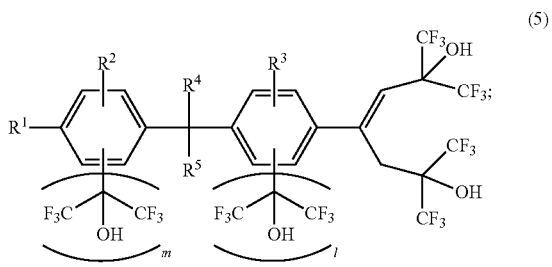

(5)

wherein an aromatic compound represented by the general formula (11):

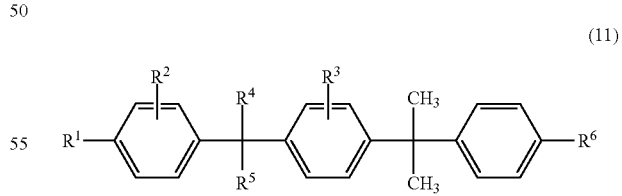

(11)

is reacted with hexafluoroacetone in the presence of an acid catalyst;
wherein $R^1$ is a hydroxyl group or an amino group; each of $R^2$ to $R^5$ is independently a hydrogen atom, a $C_{1-4}$ straight chain, or a $C_3$ or $C_4$ branched chain alkyl group, wherein hydrogen atoms of the alkyl groups may partially or totally be replaced with fluorine atoms; $R^6$ is a hydroxyl group or an amino group; and each of m and 1 is independently 0 or 1.

13. The method for producing a fluorine-containing aromatic compound as claimed in claim 8, which is represented by the general formula (6):

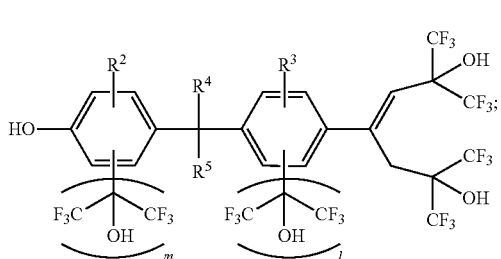

(6)

wherein an aromatic compound represented by the general formula (12):

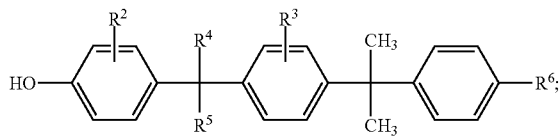

(12)

is reacted with hexafluoroacetone in the presence of an acid catalyst;

wherein each of $R^2$ to $R^5$ is independently a hydrogen atom, a $C_{1-4}$ straight chain, or a $C_3$ or $C_4$ branched chain alkyl group, wherein hydrogen atoms of the alkyl groups may partially or totally be replaced with fluorine atoms; $R^6$ is a hydroxyl group or amino group; and each of m and l is independently 0 or 1.

14. The method for producing a fluorine-containing aromatic compound as claimed in claim 13, which is represented by the formula (7):

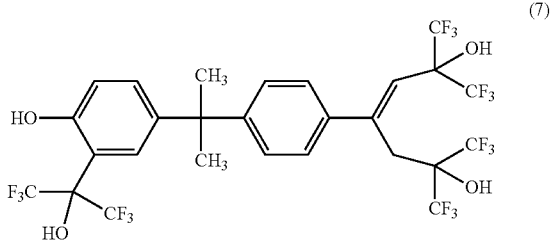

(7)

wherein an aromatic compound represented by the formula (13):

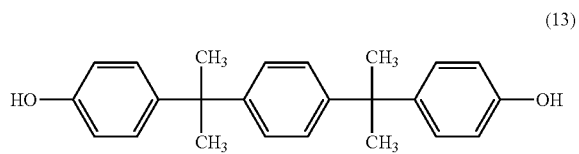 [SMILES: CC(C)(c1ccc(O)cc1)c1ccc(C(C)(C)c2ccc(O)cc2)cc1]

(13)

is reacted with hexafluoroacetone in the presence of an acid catalyst.

15. The production method as claimed in claim 8, wherein the acid catalyst is methanesulfonic acid.

* * * * *